United States Patent [19]

Franz

[11] Patent Number: 4,880,636

[45] Date of Patent: Nov. 14, 1989

[54] FILM COATED TABLET OF RANITIDINE HCL

[76] Inventor: Robert M. Franz, 8712 Mariner Dr., Raleigh, N.C. 27615

[21] Appl. No.: 194,427

[22] Filed: May 13, 1988

[51] Int. Cl.$^4$ ................................................ A61K 9/36
[52] U.S. Cl. .................................... 424/480; 424/467
[58] Field of Search ................................ 424/467, 480

[56] References Cited

U.S. PATENT DOCUMENTS

| | | | |
|---|---|---|---|
| 2,816,062 | 12/1957 | Doerr | 424/467 |
| 4,128,658 | 12/1978 | Price et al. | 514/471 |
| 4,274,830 | 6/1981 | Woznicki et al. | 424/480 X |
| 4,287,221 | 9/1981 | Tonedachi et al. | 424/480 X |
| 4,302,440 | 11/1981 | John et al. | 427/3 X |
| 4,522,840 | 6/1985 | Corfield et al. | 424/467 X |
| 4,629,620 | 12/1986 | Lindahl et al. | 424/467 X |
| 4,687,660 | 8/1987 | Baker et al. | 424/467 X |
| 4,704,285 | 11/1987 | Alderman | 424/480 X |
| 4,786,504 | 11/1988 | Forse et al. | 424/467 |
| 4,795,641 | 1/1989 | Kashdan | 424/438 |

FOREIGN PATENT DOCUMENTS

WO88/03795 6/1988 PCT Int'l Appl. .
2181052 4/1987 United Kingdom .

*Primary Examiner*—Thurman K. Page
*Attorney, Agent, or Firm*—Charles Joyner

[57] ABSTRACT

This invention relates to an improved polymeric film coating for a ranitidine Hydrocholride (HCl) tablet in which the plasticizer triacetin had been added to the polymeric film coating medium. A tablet of this invention has been found to have great stability than a tablet coating with a polymeric film which does not contain triacetin.

6 Claims, No Drawings

FILM COATED TABLET OF RANITIDINE HCL

This invention relates to an improved coated ranitidine hydrochloride (HCl) tablet and its preparation. In particular, the invention relates to the incorporation of a certain plasticizer into a film coating composition which increases the stability of the ranitidine HCl tablet and also prevents the film coating from subsequently obscuring distinctive engravings and embossments which may be present in and on the tablet's surface.

BACKGROUND OF THE INVENTION

Ranitidine, chemically identified as N-[2-[[[5-(dimethylaminomethyl-2-furanyl]methyl]thio]ethyl]-N'-methyl-2-nitro-1,1-ethenediamine (see U.S. Pat. No. 4,128,658), is a known antagonist to histamine $H_2$ receptors. This drug is widely used in the treatment of duodenal ulcers especially as the hydrochloride salt and in the form of tablets.

Film coating of tableted drug products is a process widely practiced in the pharmaceutical field. Typically this process involves spraying a solution or suspension of a polymeric material conventionally utilized for film coating purposes onto a tablet which is being tumbled in a stream of warm air. As the solvent evaporates the polymeric film coating is uniformly deposited on the tablet's surface. Film coating can be done in either aqueous or organic solvent systems, but aqueous systems are often preferred because they avoid the safety and environmental problems associated with many organic solvents. Film coating of ranitidine HCl tablets is utilized to mask the drug's bitter taste, to provide protection from destructive environmental elements, and for esthetic purposes. It is known that ranitidine HCl is subject to degradation upon aging and that such degradation is accelerated by heat, moisture and light; for example, see *Physicians' Desk Reference*, 41st ed., page 993 (1987). Further, the drug is not only extremely soluble in water (greater than 900 mg/mL at 25° C.) but is also very soluble in many commonly used organic solvents. Such high solubility and propensity to degrade in the presence of heat, moisture and light have therefore made it difficult to maintain the pharmaceutical integrity of polymeric film coated ranitidine HCl tablets.

In the art of tablet film coating, conventional plasticizing agents are frequently added to the polymeric solution or suspension to improve the flexibility of the film coating and thus minimize the filling in or covering over of engraved (cut in to the surface of the tablet) or embossed (raised above the surface) indicia and designs in the tablet face. In order to significantly retard the degradation of ranitidine HCl induced by the natural heat, moisture or light factors of the environment and to successfully mask its taste, the film coating must exceed a certain minimum thickness. Without a plasticizer this thickness can not be achieved for a tablet containing ranitidine HCl without considerable loss of the definition of the indicia and designs in or on the tablets. Preservation of such engraved or embossed indicia and designs is important not only for general appearance and trade dress purposes, but more important, to meet government requirements regarding identification of drug products.

Many of the plasticizers in common use in polymeric film coatings of pharmaceutical products, for example, polyethylene glycol, propylene glycol, dibutyl sebecate, mineral oil, sesame oil and diethyl phthalate, are unacceptable for use with ranitidine HCl tablets. Such commonly used plasticizers either tend to react with ranitidine HCl or promote degradation at the tablets' surfaces, resulting in pronounced discoloration which renders the tablets unmarketable. In addition, some conventional film coating polymers are also incompatible with ranitidine HCl and thus accelerate its degradation.

U.S. Pat. No. 4,302,440 (incorporated herein by reference and referred to hereinafter as "'440") provides a review of the art of tablet film coating, and discloses a process and formulations for film coatings of aspirin using an aqueous medium of hydroxypropyl methylcellulose (HPMC). This patent recites the difficulty of using aqueous film coating media with aspirin because of aspirin's instability in water.

While '440 teaches an HPMC film coating for aspirin which incorporates as the plasticizer of choice, triacetin, it does not teach an acceptable HPMC film coating for a tablet of ranitidine HCl. The inherent problems associated with ranitidine HCl because, for example, of its high solubility in many commonly used plasticizers, are quite different from those described for aspirin in '440. Drug dissolution and subsequent migration into the plasticized polymeric film coating after film application is a serious problem with ranitidine HCl. In the case of ranitidine HCl, the phenomenon of drug migration into the film coating, unlike in the aspirin case, occurs with polymeric films deposited from either aqueous or organic systems. Furthermore, '440 addresses degradation during the actual coating process only and makes no mention of the subsequent problem of film related degradation upon aging of the tablets which is a concern in the case of ranitidine HCl.

Patent No. '440 teaches a method for preparing a thinly coated aspirin tablet having a film of hydroxypropyl methylcellulose (HPMC) which is 0.5 to 2.0% of the dry weight of the aspirin tablet core, and 15% to 25% plasticizer, based on the dry weight of the HPMC. The term "tablet core" refers to a compressed tablet prior to coating.

It has now been found that in the case of ranitidine HCl an unacceptable thin film coating would result by applying film solids at the thickness taught in '440. While '440 teaches triacetin as the plasticizer of choice for aqueous film coating of aspirin, it also teaches the use of the alternate plasticizers, such as propylene glycol and polyethylene glycols, which are unsuitable for use with ranitidine HCl because they promote degradation. Further, unlike the aspirin tablet cores described in '440, ranitidine HCl tablet cores, because of their photosensitivity should be protected from light by the use of a colorant or opacifying agent in the film coating.

In summary, while '440 teaches a plasticizer containing aqueous film coating for aspirin tablets, it does not teach one skilled in the art of film coating a suitable film formulation, aqueous or organic solvent based, for a compressed tablet core of ranitidine HCl of composition similar to that taught in U.S. Pat. No. 4,128,658.

SUMMARY OF THE INVENTION

It has now been found that the discoloration of HPMC film coated ranitidine HCl tablets can be minimized by including triacetin (also known as triacetyl glycerol, glyceryl triacetate and 1,2,3-propanetriol triacetate) in the film. Surprisingly, a ranitidine HCl tablet coated with an HPMC film coating containing triacetin, shows a significant improvement in protection against drug migration into the film compared with a like tablet coated with similar but unplasticized HPMC films and with one coated by HPMC film coatings containing other commonly used plasticizers.

DETAILED DESCRIPTION

The present invention allows an engraved or embossed ranitidine HCl tablet core to be coated to an acceptable thickness for protection from detrimental environmental elements and for taste masking while preserving the engravings or embossments. Further, the triacetin containing film coating of this invention is essentially unreactive with the active drug, i.e., ranitidine HCl. The plasticized film coating of this invention minimizes the migration of ranitidine HCl into the coating and subsequent discoloration of the tablet. The inherent advantages of polymeric film coating including improvement of the appearance of the tablets and enhancement in the ease of swallowing of the tablets are in no way diminished by the present invention. The dissolution profile, and hence, bioavailability, of ranitidine HCl tablets bearing the triacetin containing HPMC coating of this invention remains essentially unaltered, and is comparable in this respect to similar HPMC film coated tablets without a plasticizer.

The plasticizer of the present invention, i.e., triacetin, has the following characteristics:
1. It has a high degree of compatability with the HPMC coating polymer;
2. It significantly reduces the polymer's glass transition temperature, thus improving film flexibility and definition of the tablet's engravings or embossments;
3. It is a poor solvent for ranitidine HCl (that is, a solubility of less than 0.5 mg/mL), thus minimizing drug dissolution and subsequent migration into the film coating during the coating process and thereafter, and also minimizes the concentration gradient driven drug diffusion during aging;
4. It has a relatively high boiling point (i.e., low vapor pressure) to insure the permanence of the plasticizer upon the application of heat during the coating operation;
5. It is essentially unreactive with ranitidine HCl;

An important embodiment of the present invention is an engraved or embossed ranitidine HCl tablet core uniformly coated with about 2.0 to 4.5 parts by weight of hydroxypropyl methylcellulose (HPMC) per 100 parts by weight of the ranitidine HCl tablet core, about 5% to 25% w/w (preferably 10% to 15% w/w) of triacetin as a plasticizer based on the dry weight of the HPMC, and optionally about 5% to 65% w/w (preferably 25% to 50% w/w) of a colorant or opacifying agent or agents, based on the dry weight of the HPMC. Conventional tableting ingredients such as, for example, flavoring, stabilizing, antioxidant, preserving agents and the like may be included in accordance with standard tableting practice. Furthermore, total film coating solids application to the ranitidine HCl tablet core should be between 2.1 and 5.0 (preferably between 3.0 and 4.0) parts by weight of film coating solids per 100 parts by weight of the ranitidine tablet.

The preferred HPMC used in the coating composition of the invention produces a viscosity of between 4.0 and 7.2 centipoise (cps) when measured as a 2% by weight aqueous solution at 20 degrees centigrade. Other HPMC's which yield viscosities as low as 2.4 and high as 18.0 cps when similarly measured may be satisfactorily applied. The most preferred HPMC composition is hydroxypropyl methylcellulose 2910, which is a propylene glycol ether of methylcellulose containing not less than 7.0% and not more than 12.0% hydroxypropoxy, and not less than 28.0% and not more than 30.0% methoxy, calculated on a dry basis. Acceptable coating solutions range from 1% to 20% by weight of HPMC in a solvent system, with the preferred range between 5% and 10% by weight.

Total film coating solids are applied to the tablet core in the range of between 2.1 and 5 parts by weight of dry film coating per 100 parts by weight of ranitidine HCl tablet core, with the preferred range between 3.0 and 4.0 parts by weight dry film coating per 100 parts by of the ranitidine HCl tablet core.

A variety of colorants or opacifiers may be employed in the coating solution including water soluble dyes, aluminum lakes of water soluble dyes, and inorganic pigments such as titanium dioxide and iron dioxide. The recommended range of application for suitable colorants or opacifiers is from 5% to 65% w/w based on the dry weight of the hydroxypropyl methylcellulose, with the preferred range between 25% and 50% w/w.

The preferred solvent for the film coating components is purified water, but various classes of organic solvents commonly used in this art such as alcohols, ketones, ethers and chlorinated hydrocarbons, for example, ethanol, acetone, tetrahydrofuran, methylene chloride and the like, may also be used.

The HPMC film coating may be suitably applied by conventional art methods for film coating of pharmaceutical tablets. In general, the HPMC is dispersed in purified water or other suitable solvent until dissolved followed by addition and dispersion of the desired amount of triacetin. The colorant or opacifier may then be added and intimately mixed into the dispersion. Additional components such as flavorings, stabilizers, antioxidants, and preservatives may also be added to the coating dispersion. The coating dispersion is applied to the ranitidine HCl tablet cores using standard pharmaceutical tablet coating means. Preferably, the coating dispersion is applied using air atomization spray equipment and a perforated coating pan.

EXAMPLES

The following examples are presented to further illustrate the invention and should in no way be construed as a limitation thereof.

EXAMPLE 1

A. Cast Film Plasticizer Comparison Study

Cast film studies are performed using a typical film aqueous coating composition containing, on a per gram HPMC dry weight basis, plasticizer, 0.2 gm, and Opaspray (trademark of Colorcon, Inc., West Point, PA) colorant solids 0.5 gm. Cast films are prepared by adding 1.5 g of a 15% solids solution to a uniform plate, 42 mm in diameter, and drying at ambient temperature for at least 24 hours. Ranitidine HCl (1.5 gm), of particle size 50 to 200 microns, is then spread uniformly on the dried film coating and stored at 60 degrees centigrade/78.9% relative humidity (RH) for approximately two weeks. The RH is controlled by using a desiccator jar and a saturated KBr solution, which is maintained at 60° C. in a drying oven. This procedure is used to prepare films containing triacetin, triethyl citrate, polyethylene glycol (PEG) 400, propylene glycol and glycerol as the plasticizer. After two weeks, the cast films are removed and visually examined for discoloration. The results of this study are shown in Table 1.

TABLE 1

Summary of Ranitidine HCl/Plasticizer Study

| Plasticizer | Molecular Weight (G/Mol) | Boiling Point (Deg C.) | Ranitidine HCl Solubility mg/ml | Cast Film Discoloration |
|---|---|---|---|---|
| Triacetin | 218.20 | 258 | 0.042 | 1[b] |
| Triethyl Citrate | 276.28 | 294 | 0.183 | 3 |
| PEG 400 | 380–420 | 238[a] | 5.17 | 4 |
| Propylene Glycol | 76.09 | 188 | 196.5 | 2 |
| Glycerol | 92.09 | 290 | 307.2 | 5 |

[a]Flash Point
[b]1 = least discoloration, 5 = greatest discoloration

B. Retarding of Ranitidine HCl Tablet Discoloration with Triacetin

Four batches of ranitidine HCl tablet cores are coated using a procedure according to that described in example 2, vide infra. The coating composition of each batch contained Opaspray Pink M-1-1457 as the colorant, and the amount of triacetin varies from 0% to 15% (by 5% increments). All of the tablet cores are coated at the level of 2.5 parts total film solids per 100 parts by weight of the ranitidine tablet core. Tablets are stored for 1 month in high density polyethylene bottles at 60° C./78.9% RH and then visually examined for appearance changes, i.e, the darker the appearance, the greater the decomposition. The results of this study are shown in Table 2.

TABLE 2

Summary of triacetin level effects on HPMC coated tablet appearance after storage in HDPE bottles at 60° C./78.9% RH for 30 days

| Triacetin Level | Appearance[a] |
|---|---|
| 0% | 4 |
| 5% | 3 |
| 10% | 2 |
| 15% | 1 |

[a]1 = least decomposition
4 = greatest decomposition

EXAMPLE 2

Hydroxypropyl methylcellulose, 6 cps, 24.24 g, is agitated in approximately 150.00 g of hot purified water. Cold purified water, 124.43 g, is added with agitation to dissolve the polymer. Upon complete dissolution of the hydroxypropyl methylcellulose, the solution is allowed to cool to ambient conditions. Triacetin, 3.65 g, is added to the polymer solution and dispersed. Colorant suspension, 31.01 g, in the form of an Opaspray White M-1-7120 (trademark) colorant suspension (Colorcon Inc., West Point, PA) which contains 39.1% solids by weight is then added and dispersed in the HPMC/triacetin solution. The resulting coating solution has the following composition:

| INGREDIENTS | % w/w |
|---|---|
| Hydroxypropyl methylcellulose 6 cps | 7.3 |
| Triacetin | 1.1 |
| colorant suspension | 9.3 |
| Purified Water | 82.3 |

| INGREDIENTS | % w/w |
|---|---|
| | 100.0 |

Embossed (raised indicia), uncoated ranitidine HCl tablet cores containing the equivalent of 150 mg of the free base are prepared by mixing the active ingredient with a pharmaceutically suitable binder and lubricant and compressing the mixture into tablet cores weighing 300 mg each in a manner similar to that taught in U.S. Pat. No. 4,128,658. One kg of the uncoated tablet cores are placed in an HCT 30 HI COATER (trademark) perforated coating pan (Vector Corp., Marion, IA). The coating solution is applied using an air atomizing nozzle. Twelve milligrams of film coating solids are applied per tablet. The embossed indicia are essentially as distinct and easy to read as those on the uncoated tablet core. The tablets are found to be substantially free of discoloration after prolonged periods of storage under normal conditions.

EXAMPLE 3

Hydroxypropyl methylcellulose, 27.6 g, 6 cps is agitated in a combination of 136.9 g of isopropyl alcohol and 319.9 g of dichloromethane until dissolved. Triacetin, 4.1 g, is added to the polymer solution and dispersed. Colorant suspension (Opaspray Apricot K-1-1173), 22.5 g, containing 37% w/w solids is then added and dispersed in the solution. The resulting coating solution has the following composition:

| INGREDIENTS | % w/w |
|---|---|
| Hydroxypropyl methylcellulose | 5.4 |
| Triacetin | 0.8 |
| Colorant suspension | 4.4 |
| Isopropyl alcohol | 26.8 |
| Dichloromethane | 62.6 |
| | 100.0 |

Engraved (indicia cut 0.254 mm into the surface), 300 mg ranitidine HCl tablet cores containing the equivalent of 150 mg of free base are prepared by the method described in example 2. One kg of the uncoated tablets are placed in an HCT 30 HI COATER coating pan. The coating solution is applied using an air atomizing nozzle. Twelve milligrams of film coating solids are applied per tablet. The engraving is substantially free of edge erosion and filling in and the coated tablets are found to be substantially free of discoloration after a prolonged period of normal storage.

I claim:
1. A ranitidine HCl tablet coated with a polymeric film comprising; hydroxypropyl methylcellulose (HPMC), 5% to 25% (based on the weight of said HPMC) triacetin and optionally 5% to 65% (based on the weight of said HPMC) colorant or opacifying agent.
2. A tablet of claim 1 wherein the polymeric coat is in the range of 2.1 to 5.0 parts by weight per 100 parts by weight of the tablet.
3. A tablet of claim 1 wherein the polymeric coat is in the range of 3.5 to 4.5 parts by weight per 100 parts by weight of the tablet.
4. A tablet of claim 1 wherein the polymeric film coating also contains one or more opacifying agents.
5. A tablet of claim 1 wherein the polymeric film coating also contains one or more colorants.
6. A tablet of claim 1 wherein the polymeric film coating also contains one or more colorants and one or more opacifying agents.

* * * * *